United States Patent

Tronich et al.

Patent Number: 5,292,932
Date of Patent: Mar. 8, 1994

[54] PROCESS FOR THE PREPARATION OF 5-CHLORO-2-HYDROXY-4-ALKYL-BENZENESULFONIC ACIDS

[75] Inventors: Wolfgang Tronich, Eppstein/Taunus; Carl-Stephan Fröhlich, Kriftel; Gunther Sell, Kronberg, all of Fed. Rep. of Germany

[73] Assignee: Hoechst Aktiengesellschaft, Frankfurt am Main, Fed. Rep. of Germany

[21] Appl. No.: 829,081

[22] PCT Filed: Aug. 11, 1990

[86] PCT No.: PCT/EP90/01324
§ 371 Date: Apr. 10, 1992
§ 102(e) Date: Apr. 10, 1992

[87] PCT Pub. No.: WO91/02717
PCT Pub. Date: Mar. 7, 1991

[30] Foreign Application Priority Data

Aug. 18, 1989 [DE] Fed. Rep. of Germany ....... 3927258

[51] Int. Cl.$^5$ ............................................. C07C 309/30
[52] U.S. Cl. ....................................... 562/78; 562/73; 568/709
[58] Field of Search ............................. 562/78, 74, 73; 568/709

[56] References Cited

U.S. PATENT DOCUMENTS 3,903,178 9/1975 Nakamura et al.

OTHER PUBLICATIONS

Sandler et al., "Organic Functional Group Preparations", Academic Press, New York, 1968, pp. 81–82.

Primary Examiner—Nicky Chan

[57] ABSTRACT

Process for the preparation of compounds of the formula (1)

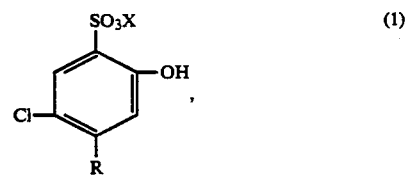

in which R is an alkyl ($C_1$–$C_6$) group and X is a hydrogen or alkali metal atom, in which compounds of the formula (2)

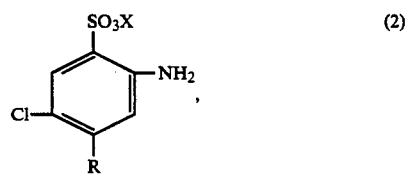

in which R and X have the abovementioned meanings, are converted into the corresponding diazonium compound with a diazotizing agent in a mineral acid at temperatures of about −5° C. to about +25° C., this diazonium compound is then reacted, without or after intermediate isolation, with aqueous mineral acid at temperatures of about 70° C. to about 120° C. and the resulting compounds of the above formula (1) are isolated.

20 Claims, No Drawings

PROCESS FOR THE PREPARATION OF 5-CHLORO-2-HYDROXY-4-ALKYL-BENZENE-SULFONIC ACIDS

DESCRIPTION

The present invention relates to a process for the preparation of 5-chloro-2-hydroxy-4-alkyl-benzenesulfonic acids which has been improved over the prior art.

5-Chloro-2-hydroxy-4-alkyl-benzenesulfonic acids, in particular 5-chloro-2-hydroxy-4-methylbenzenesulfonic acid and 5-chloro-2-hydroxy-4-ethylbenzenesulfonic are important precursors for the preparation of 3,5-dichloro-2-hydroxy-4-alkyl-1-nitrobenzenes, in particular 3,5-dichloro-2-hydroxy-4-methyl-1-nitrobenzene and 3,5-dichloro-2-hydroxy-4-ethyl-1-nitrobenzene, which in turn are used as intermediate products for the production of color couplers for color papers (German Offenlegungsschrift 2,216,804 and European Patent 175,151).

It is known from German Offenlegungsschrift 2,216,804 and German Offenlegungsschrift 2,501,899, for example, that 5-chloro-2-hydroxy-6-methylbenzenesulfonic acid can be obtained by sulfonation of 4-chloro-5-methylphenol, and this product can be converted into 3,5-dichloro-2-hydroxy-4-methyl-i-nitrobenzene by chlorination and desulfonating nitration, likewise in a known manner.

According to Japanese Patent 61/57536 (8/84) (FUJI), for example, 5-chloro-2-hydroxy-4-ethylbenzenesulfonic acid is obtained in an analogous manner from 4-chloro-5-ethylphenol, and this product can then likewise be converted into 3,5-dichloro-2-hydroxy-4-ethyl-1-nitrobenzene by chlorination and desulfonating nitration.

However, a decisive disadvantage of these known processes for the preparation of 5-chloro-2-hydroxy-4-alkylbenzenesulfonic acids, as described in detail in German Offenlegungsschrift 3,431,687, pages 4 and 5, is above all the difficult accessibility of the 4-chloro-5-alkylphenols required as starting compounds.

It has now been found that 5-chloro-2-hydroxy-4-alkyl($C_1$-$C_6$)-benzenesulfonic acids of the general formula (1)

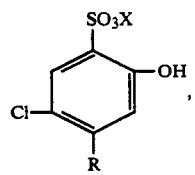
(1)

in which R is an alkyl($C_1$-$C_6$) group, preferably a methyl or ethyl group, and X is a hydrogen atom or an alkali metal atom, preferably a sodium atom, can be prepared in good yields and in a high purity, avoiding the disadvantages of the known processes of the difficult accessibility of the 4-chloro-5-alkylphenols required as starting compounds in those processes, by converting 5-chloro-2-amino-4-alkyl($C_1$-$C_6$)-benzenesulfonic acids of the general formula (2)

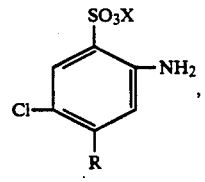
(2)

in which R and X have the abovementioned meanings, into the corresponding diazonium compound using a diazotizing agent in a mineral acid at temperatures of about −5° C. to about +25° C., preferably about +5° C. to about +20° C., subsequently reacting this diazonium compound, without or after, preferably without, intermediate isolation, with aqueous mineral acid at temperatures of about 70° C. to about 120° C., preferably about 100° C. to about 115° C,. and isolating the resulting compounds of the above formula (1).

The process according to the invention can be represented by the following equation:

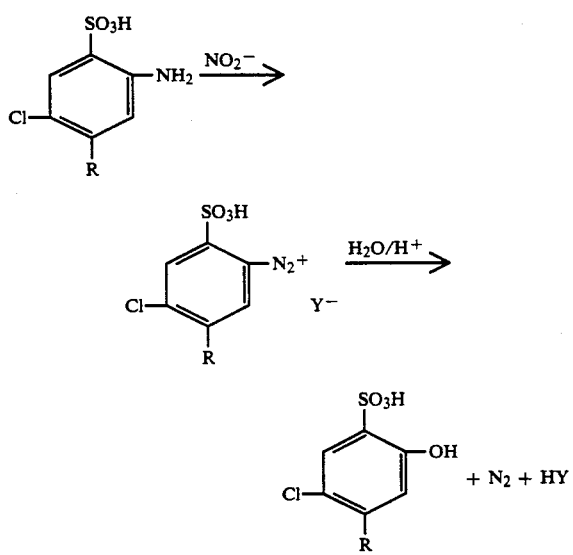

In this equation, R has the meaning given above and $Y^-$ is any desired anion, preferably $-SO_4H^-$, $\frac{1}{2}SO_4^-$ or $Cl^-$.

The diazotization of the 5-chloro-2-amino-4-alkylbenzenesulfonic acids is in general carried out in sulfuric acid or hydrochloric acid, aqueous acids preferably being employed in the concentrations customary for such reactions. An approximately 20 to approximately 70% strength aqueous sulfuric acid or an approximately 5 to approximately 30% strength aqueous hydrochloric acid, for example, is usually used. However, acid concentrations outside these concentration ranges can also be employed. The diazotization agents used are the compounds customary for this reaction, such as, for example, alkali metal nitrites or nitrosylsulfuric acid. Preferably, sodium nitrite is employed in the form of an aqueous solution.

The diazotization temperature and duration of the diazotization correspond to the customary conditions for such reactions and are in general between −5° C. and about 25° C. on the one hand and between one and several hours on the other hand. The concentration ratios are likewise not particularly critical, but are usually chosen so that the diazonium salt formed is present in dissolved form or as a stirrable suspension after the reaction. When the diazotization has ended (for example using alkali metal nitrites), the nitrite which is in general employed in a slight excess and has not been consumed is destroyed by addition of, for example, sulfamic acid.

The diazonium compound is usually converted into the corresponding 5-chloro-2-hydroxy-4-alkyl($C_1$-$C_6$)-benzenesulfonic acid by introducing the aqueous solution or suspension of the diazonium compound into aqueous mineral acid at elevated temperature. Aqueous mineral acid—preferably aqueous sulfuric acid—is usually used as the mineral acid for this reaction, which is known as "phenol cooking", the acid concentration being in the range customary for such reactions, for example between about 30 and about 80% strength sulfuric acid.

The reaction temperature in this reaction is in general between about 70° and about 120° C., preferably between about 100° C. and about 115° C. When the evolution of nitrogen has ended, the reaction mixture is advantageously cooled to a temperature below 20° C., in particular below 15° C., and the crystalline reaction product is isolated. The 5-chloro-2-hydroxy-4-alkyl(-$C_1$-$C_6$)-benzenesulfonic acids can be obtained as free acids or preferably as alkali metal salts, preferably as the sodium salts of the sulfonic acids, depending on the nature of the diazotizing agent employed and the working-up conditions.

It is to be regarded as surprising that the 5-chloro-2-amino-4-alkylbenzenesulfonic acids can be prepared in good yields and in a high purity by the reaction known as "phenol cooking" without the resin formation which often occurs during this reaction and without the formation of organic impurities which are difficult to remove.

The 5-chloro-2-amino-4-alkyl($C_1$-$C_6$)-benzenesulfonic acids are products which are readily accessible industrially. Thus, for example, 5-chloro-2-amino-4-methyl-benzenesulfonic acid is a product which is available industrially in large amounts from toluene-4-sulfonic acid. 5-Chloro-2-amino-4-ethyl-benzenesulfonic acid can be prepared by a process which is in principle the same as that for the methyl compound, i.e. starting from ethylbenzene-4-sulfonic acid (in this context, compare Winnacker-Küchler: Chemische Technologie (Chemical Technology), volume 6, 4th edition, page 162 (1982)).

The 5-chloro-2-hydroxy-4-alkyl ($C_1$-$C_6$) -benzenesulfonic acids isolated or their alkali metal salts can be chlorinated in aqueous sulfuric acid by processes which are known per se to give the 3,5-dichloro-2-hydroxy-4-alkyl($C_1$-$C_6$)-benzenesulfonic acids, and these can then be converted by means of nitric acid, likewise in a known manner, into 3,5-dichloro-2-hydroxy-4-alkyl(-$C_1$-$C_6$)-1-nitrobenzenes (intermediate products for the preparation of color couplers for color papers).

However, it is also possible for the 5-chloro-2-hydroxy-4-alkyl($C_1$-$C_6$)-benzenesulfonic acids obtained by the process according to the invention to be converted directly into 3,5-dichloro-2-hydroxy-4-alkyl-1-nitrobenzenes without intermediate isolation, for example by chlorination and subsequent nitration in accordance with German Patent 2,501,899.

The following examples serve to illustrate the process according to the invention, without limiting it thereto.

EXAMPLE 1

Sodium 5-chloro-2-hydroxy-4-methyl-benzenesulfonate 101 parts of a 38% strength aqueous solution of sodium nitrite are added dropwise to a solution of 110.8 parts of 5-chloro-2-amino-4-methyl-benzenesulfonic acid in 440 parts of approximately 22% strength aqueous sulfuric acid at 15° C. in the course of about 2 hours, while stirring. After the mixture has been subsequently stirred for about 30 minutes, excess nitrite is destroyed with about 3 parts of a saturated aqueous solution of sulfamic acid.

The resulting suspension of 5-chloro-2-diazonium-4-methyl-benzenesulfonic acid is now introduced, in the course of about 2 hours and with intensive stirring, into 600 parts of hot approximately 64% strength aqueous sulfuric acid which has a temperature of 110° C. The mixture is subsequently stirred at about 100° C. for about 1 hour and is allowed to cool to about 15° C., while stirring, and the sodium salt of 5-chloro-2-hydroxy-4-methyl-benzenesulfonic acid is filtered off. After washing with about 2×200 parts of an approximately 6% strength sodium sulfate solution and drying in a vacuum cabinet, 110 parts of sodium 5-chloro-2-hydroxy-4-methyl-benzenesulfonate are obtained in a purity of about 92%, which corresponds to a yield of 83% of theory. The remaining 8% consists of inorganic salts, essentially sodium sulfate.

The sodium salt can also be isolated by first adding saturated sodium chloride solution or sodium sulfate solution to the suspension which has been cooled to about 15° C., and then filtering off the product with suction.

A sample recrystallized from water shows the following analytical values: $C_7H_6ClNaSO_4$ (244.63)

|  | C | H | S | Cl |
| --- | --- | --- | --- | --- |
| calculated (%) | 34.3 | 2.45 | 13.1 | 14.3 |
| found (%) | 34.4 | 2.3 | 13.0 | 14.4 |

EXAMPLE 2

Sodium 5-chloro-2-hydroxy-4-ethyl-benzenesulfonate 101 parts of a 38% strength aqueous sodium nitrite solution are added dropwise to a solution of 118 parts of 5-chloro-2-amino-4-ethyl-benzenesulfonic acid (prepared, for example, by a process analogous to that known for 5-chloro-2-amino-4-methyl-benzenesulfonic acid) in 400 parts of approximately 24% strength aqueous sulfuric acid at 15° C. in the course of 4 to 5 hours, while stirring. Excess nitrite is destroyed with about 3 parts of a saturated aqueous solution of sulfamic acid.

The resulting suspension of the diazonium compound of 5-chloro-2-amino-4-ethyl-benzenesulfonic acid is now introduced, in the course of about 2 hours and with intensive stirring, into 600 parts of hot approximately 64% strength aqueous sulfuric acid which has a temperature of 110° C. The mixture is subsequently stirred for about 1 hour and is then allowed to cool to about 15° C., while stirring, and the sodium salt of 5-chloro-2-hydroxy-4-ethyl-benzenesulfonic acid is filtered off. After washing with 3×200 parts of a cold approximately 6% strength sodium sulfate solution and drying in a vacuum cabinet, 95 parts of sodium 5-chloro-2-amino-4-ethyl-benzenesulfonate are obtained in a purity of 96%, which corresponds to a yield of 70% of theory.

The remaining 4% consists of inorganic salts, essentially sodium sulfate.

The product can also be isolated by salting out with sodium chloride or sodium sulfate, analogously to Example 1.

A sample recrystallized from water has the following analytical values: $C_8H_8ClNaSO_4$ (258.65)

|  | C | H | S | Cl |
|---|---|---|---|---|
| calculated (%) | 37.1 | 3.1 | 12.4 | 13.7 |
| found (%) | 37.5 | 3.0 | 12.1 | 13.7 |

EXAMPLE 3

Sodium 5-chloro-2-hydroxy-4-methyl-benzenesulfonate 101 parts of an approximately 38% strength aqueous sodium nitrite solution are added dropwise to a solution of 110.8 parts of 5-chloro-2-amino-4-methyl-benzenesulfonic acid in 440 parts of approximately 6% strength aqueous hydrochloric acid at 15° C. in the course of about 2 hours. After about 30 minutes, about 3 parts of a saturated aqueous sulfamic acid solution are added to destroy excess nitrite.

The resulting suspension of the diazonium salt is now introduced, in the course of about 2 hours and with intensive stirring, into 600 parts of hot approximately 66% strength aqueous sulfuric acid which has a temperature of about 110° C.

The reaction mixture is subsequently stirred at about 100° C. for about 1 hour and then cooled to about 15° C. and the sodium salt of 5-chloro-2-hydroxy-4-methyl-benzenesulfonic acid is filtered off. After washing with an approximately 6% strength sodium sulfate solution, a product is obtained which corresponds in yield and purity to that of Example 1, with the difference that the inorganic salt content essentially consists of a mixture of sodium sulfate and sodium chloride.

EXAMPLE 4

The procedure is analogous to Example 3, but with the difference that the diazotization is carried out in 350 parts of approximately 41% strength sulfuric acid instead of in hydrochloric acid and the subsequent "cooking" of the diazonium salt suspension is carried out in 800 parts of approximately 50% strength sulfuric acid instead of in 600 parts of approximately 66% strength sulfuric acid.

After working-up of the reaction mixture, a product is obtained which corresponds to Example 1 in respect of yield and purity.

We claim:

1. A process for the preparation of a compound of the formula (1)

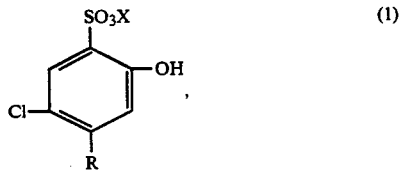

(1)

in which R is an alkyl ($C_1$-$C_6$) group and X is a hydrogen or alkali metal atom, which comprises converting a compound of the formula (2)

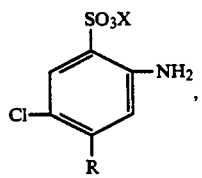

(2)

in which R and X have the abovementioned meanings, into the corresponding diazonium compound with a diazotizing agent in a mineral acid at temperatures of about −5° C. to about +25° C., subsequently reacting this diazonium compound, without or after intermediate isolation, with aqueous mineral acid at temperatures of about 70° C. to about 120° C. to obtain the compound of the above formula (1).

2. The process as claimed in claim 1, wherein R in the formulae (1) and (2) is a methyl or ethyl group.

3. The process as claimed in claim 1, wherein X in the formulae (1) and (2) of claim 1 is an alkali metal atom.

4. The process as claimed in claim 1, wherein the conversion into the diazonium compound is carried out in aqueous sulfuric acid or aqueous hydrochloric acid as the mineral acid.

5. The process as claimed in claim 1, wherein an alkali metal nitrite or nitrosylsulfuric acid is used as the diazotizing agent.

6. The process as claimed in claim 1, wherein an aqueous solution of sodium nitrite is used as the diazotizing agent.

7. The process as claimed in claim 1, wherein the conversion into the diazonium compound is carried out at temperatures of about 5° C. to about 20° C.

8. The process as claimed in claim 1, wherein the reaction of the diazonium compound with the aqueous mineral acid is carried out at temperatures of about 100° C. to about 115° C.

9. The process as claimed in claim 1, wherein the reaction of the diazonium compound is carried out with aqueous sulfuric acid.

10. The process as claimed in claim 1 which includes the step of isolating said compound of formula (1 from said aqueous mineral acid by crystallization.

11. The process as claimed in claim 10, wherein the isolation of said compound of formula (1) is provided by cooling until crystallization occurs, optionally followed by filtration or by salting out with sodium chloride or sodium sulfate.

12. The process as claimed in claim 1, wherein:
R in the formulae (1) and (2) is a methyl or ethyl group, and
X in the formulae (1) and (2) is a sodium atom.

13. The process as claimed in claim 1, wherein said mineral acid in which the conversion to the diazonium compound takes place is aqueous sulfuric acid or aqueous hydrochloric acid, and the temperature at which said conversion takes place is in the range of about 5° to 20° C.;
the diazotizing agent is an alkali metal nitrite or nitrosylsulfuric acid; and
the reaction of the diazonium compound with the aqueous mineral acid is carried out with sulfuric acid as the aqueous mineral acid.

14. The process as claimed in claim 13, wherein the diazotizing agent is an aqueous solution of sodium nitrite.

15. The process as claimed in claim 2, wherein said mineral acid in which the conversion to the diazonium compound takes place in aqueous sulfuric acid or aqueous hydrochloric acid, and the temperature at which said conversion takes place is in the range of about 5° to 20° C.;
  the diazotizing agent is an alkali metal nitrite or nitrosylsulfuric acid; and
  the reaction of the diazonium compound with the aqueous mineral acid is carried out with sulfuric acid as the aqueous mineral acid.

16. The process as claimed in claim 2, wherein the reaction of the diazonium compound with the aqueous mineral acid is carried out at a temperature between about 100° and about 115° C.

17. The process as claimed in claim 15, wherein the reaction of the diazonium compound with the aqueous mineral acid is carried out at a temperature between about 100° and 115° C.

18. A process for the preparation of a 3,5-dichloro-2-hydroxy-4-($C_1$–$C_6$)-alkyl-1-nitrobenzene, comprising the steps of:
  carrying out the process as claimed in claim 1, thereby obtaining said compound of formula (1);
  chlorinating said compound of formula (1); and nitrating the product of said chlorinating step to obtain the 3,5-dichloro-2-hydroxy-4-($C_1$–$C_4$)-alkyl-1-nitrobenzene.

19. The process as claimed in claim 18, wherein said chlorinating step is carried out on said compound of formula (1) without first isolating said compound of formula (1).

20. The process as claimed in claim 3, wherein said alkali metal atom is a sodium atom.

* * * * *